(12) United States Patent
Chuang et al.

(10) Patent No.: US 8,466,302 B1
(45) Date of Patent: Jun. 18, 2013

(54) PROCESS FOR PRODUCING PROPYLENE OXIDE

(75) Inventors: Karl T. Chuang, Edmonton (CA); Christina Dirk-Faitakis, Edmonton (CA); Tzong-Bin Lin, Chia-Yi (TW); Hung-Chung Shen, Chia-Yi (TW)

(73) Assignee: CPC Corporation, Taiwan, Taipei (TW)

( * ) Notice: Subject to any disclaimer, the term of this patent is extended or adjusted under 35 U.S.C. 154(b) by 0 days.

(21) Appl. No.: 13/332,741

(22) Filed: Dec. 21, 2011

(51) Int. Cl.
*C07D 301/14* (2006.01)

(52) U.S. Cl.
USPC ............................................. 549/525

(58) Field of Classification Search
USPC ................................................. 549/525
See application file for complete search history.

(56) References Cited

U.S. PATENT DOCUMENTS

| | | | |
|---|---|---|---|
| 2,785,185 A | 3/1957 | Phillips | |
| 2,804,473 A | 8/1957 | Phillips | |
| 3,341,556 A | 9/1967 | Stautzenberger | |
| 3,476,776 A * | 11/1969 | Erpenbach et al. | 549/525 |
| 3,663,574 A | 5/1972 | Yamagishi | |
| 5,679,872 A | 10/1997 | Streicher | |
| 6,087,513 A | 7/2000 | Liao | |
| 6,358,373 B1 | 3/2002 | Leemann | |
| 7,332,095 B2 | 2/2008 | Johnston | |
| 7,667,068 B2 | 2/2010 | Miller | |
| 7,857,944 B2 | 12/2010 | Hsiao-Ping | |
| 7,985,867 B2 | 7/2011 | Fan | |
| 2006/0161010 A1 | 7/2006 | Gobbel | |

FOREIGN PATENT DOCUMENTS

| | | |
|---|---|---|
| GB | 1076288 A | 7/1967 |
| WO | 2011/012969 A2 | 2/2011 |

OTHER PUBLICATIONS

Yamagishi et al, Make Propylene Oxide Direct, 1976, Hydrocarbon Processing(1966-2001), 55(11), p.102-104, (abstract page).*
PCT/US2012/033354 Int'l Search Report and Written Opinion Aug. 2, 2012.
M. Kotora et al: Modelling of Reactive Distillation-Propylene Oxide Production: Petroleum & Coal vol. 47, No. 21 (Jan. 1, 2005) M pp. 26-38, XP55030146.

* cited by examiner

*Primary Examiner* — Taylor Victor Oh
(74) *Attorney, Agent, or Firm* — Cascio & Zervas (57) ABSTRACT

A continuous epoxidation process for the production of high purity propylene oxide by the reaction of propylene with an oxidant that is a per-acid, such as peracetic acid (PAA), in a reactive distillation (RD) column. The RD column provides excellent heat integration and temperature control, and the process has the advantage of lower investment cost for capital equipment. The process operates at mild temperatures and pressures. A ferric acetylacetonate homogeneous catalyst and/or stabilizer may be included as part of the PAA feed to the process to increase PAA conversion and selectivity to propylene oxide. A pre-reactor can be incorporated upstream of the RD column to increase the residence time at lower temperatures to enhance productivity.

25 Claims, 3 Drawing Sheets

PROCESS FOR PRODUCING PROPYLENE OXIDE

FIELD OF THE INVENTION

The present invention relates generally to the manufacture of propylene oxide by reacting propylene with a per-acid oxidant and more particularly to a continuous epoxidation process of reacting propylene with peracetic acid in a reactive distillation column.

BACKGROUND OF THE INVENTION

Propylene oxide (PO) is a versatile and useful commodity chemical. By volume, PO is among the top 50 chemicals produced in the world and is used primarily as an intermediate in the production of polyurethanes, propylene glycol, polyglycols, glycol ethers, allyl alcohols, and isopropanolamines. PO currently is manufactured by two main commercial processes: the chlorohydrin process and the hydroperoxide process.

In the chlorohydrin propylene oxide (CHPO) process, propylene and chlorine react in the presence of water to produce the two isomers of propylene chlorohydrin. This is followed by dehydrochlorination with lime or caustic to PO and the corresponding salt. A significant drawback of the chlorohydrin process is the large volume of water effluent (about 40 times the volume of PO produced), containing calcium chloride and/or sodium chloride along with other chlorinated organics. As a result, the technology is considered obsolete and only the hydroperoxide process is employed in newer PO production plants.

The hydroperoxide process, also referred to as indirect oxidation, proceeds via a two-step process: The first step requires the formation of a peroxide that is either hydrogen peroxide or an organic peroxide. In the second step the hydrogen peroxide is converted to water, or the organic peroxide is converted to the corresponding alcohol or acid, by epoxidation of propylene to PO. The two major routes responsible for the majority of current global production of PO are the propylene oxide/tert-butyl alcohol (PO/TBA) and the propylene oxide/styrene monomer (PO/SM) co-product processes. In both cases the co-products are formed in larger amounts than the PO itself, and therefore the economic viability of each route relies on co-product value and market demand.

Another technique for propylene oxide production is the cumene hydroperoxide route that is described as a co-product free hydroperoxidation route to PO and uses cumene hydroperoxide (CHP) as the oxidant. Co-product production is avoided by dehydrating and hydrogenating the cumyl alcohol, produced from the oxidation of propylene, back to cumene for reused.

Current industrial techniques for PO manufacture are deficient in a number of respects including: formation of undesirable by-products, propensity for PO to decompose and requirements for costly purification procedures. Both the chlorohydrin and the hydroperoxide processes are indirect processes. To date no direct oxidation process, i.e. reaction of propylene with oxygen, for PO manufacture has been commercialized. Severe technological limitations were shown to exist in prior attempts to create a direct oxidation process, including poor propylene conversion and selectivity.

Various peracetic acid epoxidation of propylene techniques are known. For example, U.S. Pat. No. 2,785,185 to Phillips et al, describes making oxirane compounds from olefins and aldehyde monoperacylates wherein PO is made by reacting propylene with an acetaldehyde monoperacetate in the presence of a catalyst in acetone solution in an autoclave reactor operating at 90° C. under pressure. The reactor material was then fractionally distilled to produce PO at a conversion of 43%, based on acetaldehyde monoperacetate. U.S. Pat. No. 3,341,556 to Stautzenberger and Richey describes a process for the production of PO by reaction of peracetic acid and propylene in the presence of a catalyst in an inert solvent. The reaction proceeds in a stainless steel autoclave reactor with reaction products separated by distillation. Finally, U.S. Pat. No. 3,663,574 to Yamagishi et al., describes the so-called The Daicel process for the continuous production of propylene oxide that involves bubbling propylene gas into an organic solvent solution containing 25% (by weight) peracetic acid and a stabilizer (tributyl phosphate) through a series of reaction columns. PO is separated from the liquid reaction mixture by absorption into butanol. In the Daicel process, no catalyst was used for epoxidation.

SUMMARY OF THE INVENTION

The present invention is based in part on the demonstration that high purity propylene oxide can be produced by epoxidation of propylene with an oxidant such as peracetic acid (PAA) in a reactive distillation (RD) column. The epoxidation reaction and the distillation take place simultaneously. Implementing both reaction and distillation in the RD column results in savings of capital equipment. In addition, the heat from exothermic reaction enables the reduction of reboiler duty in the distillation process. Modeling based on experimental kinetic data confirmed the validity of the mechanism derived from the experimental results.

In one aspect, the invention is directed to a process for continuous epoxidation of propylene to produce propylene oxide in a vertical column by reactive distillation that includes the steps of:

(a) feeding propylene into the vertical column which includes a feed zone, a top zone and a bottom zone, (b) feeding peracetic acid and solvent such as ethyl acetate into the vertical column;

(c) concurrently in the vertical column, reacting the propylene and peracetic acid to form propylene oxide in the presence of a homogeneous catalyst and recovering a mixture containing propylene oxide, acetic acid and solvent as a bottoms fraction from the bottom zone;

(d) introducing the mixture into a first distillation zone, from which an acetic acid rich stream is recovered from the bottom and a propylene oxide rich stream is recovered from the overhead; and (e) introducing the propylene oxide rich stream into a second distillation zone and recovering a distillate stream rich in propylene, a middle stream rich in propylene oxide, and a bottoms stream rich in the solvent (ethyl acetate).

The reaction is preferably conducted in an inert solvent and in the presence of a homogeneous metal ion catalyst. A pre-reactor can be positioned upstream of the vertical column to increase the residence time of the propylene and peracetic acid. It has been shown that a particularly preferred source of the peracetic acid is derived by oxidation of acetaldehyde in an inert solvent and metal ion catalyst. Previous difficulties encountered with the PAA route were attributed to instability of the PAA at high temperatures. This was usually attributed to the result of the large amount of heat liberated from the epoxidation reaction coupled with poor temperature control of the reactor.

BRIEF DESCRIPTION OF THE DRAWINGS

Throughout the drawings, like reference numerals will be understood to refer to like parts and components.

DETAILED DESCRIPTION OF THE PREFERRED EMBODIMENTS

Epoxidation Reaction

The formation of epoxides by the reaction of alkenes with per-acids is the well-known Prilezhaev reaction and the reaction scheme for PO formation from propylene and PAA is as follows: peracetic acid+propylene→acetic acid+propylene oxide. In this reaction, one mole of PAA reacts with one mole of propylene to yield one mole of PO and one mole of the corresponding carboxylic acid, namely, acetic acid. The acetic acid is recovered as a co-product and the solvent can be recycled for use in PAA production. PAA is the preferred epoxidizing agent because the market for acetic acid is very large. The only significant side reaction is the decomposition of PAA: peracetic acid→acetic acid+oxygen. As with the primary reaction, this side reaction also generates acetic acid as a co-product, but the side-reaction nevertheless should be minimized in order to maximize the PO yield. Other side reactions and byproducts can be minimized by judicious choice of the PAA feed (or the production process of the PAA) as further described herein.

System for Epoxidation in a Reactive Distillation Column

Figure 1:
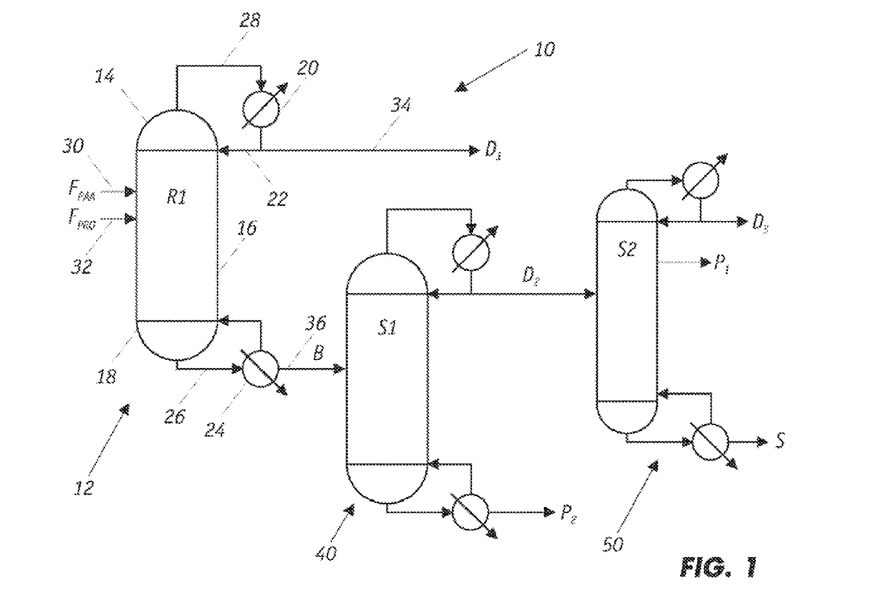
FIG. 1 is a schematic flow diagram of a reactive distillation process for producing propylene oxide.

FIG. 1 depicts a system 10, for the continuous epoxidation of propylene with peracetic acid to manufacture propylene oxide, which includes a reactive distillation column (R1) 12, a first distillation column (S1) 40 and a second distillation column (S2) 50. As described herein, the epoxidation in RD column 12 yields a distillate $D_1$ that comprises volatiles that can be recycled and a bottoms product B that is further processed in the two distillation columns to recover high purity propylene oxide, co-product acetic acid, volatiles and other products.

RD column 12 has an upper first portion 14, a middle second portion 16 and a lower third portion 18. A condenser 20 condenses condensable components in the gas phase reaction mixture 28 for their partial return as liquids 22 to the first portion 14 of RD column 12. The reflux flow returns the liquid onto the stage below the condenser 20. The remaining portion of the condensate from the condenser leaves as distillate product $D_1$ through stream 34. A reboiler 24 vaporizes the more volatile components of the liquid reaction mixture 26 for their return as liquids to the third portion 18 of RD column 12. The vapor is returned onto the first stage above the reboiler 24. A portion of the liquid reaction mixture leaves the reboiler as bottoms product B via stream 36. RD column 12 is preferably a bubble column or a tray column, where the propylene bubbles through the liquid reaction mixture. Alternatively, the RD column can consist of a packed column where vapor-liquid contact is provided by the packing surface.

PAA is fed as a solution in an inert solvent to RD column 12 via first feed line ($F_{PAA}$) 30 and propylene is fed via second feed line ($F_{PRO}$) 32. Each of the first and second feed lines 30 and 32 enters the middle second portion 16 preferably at a stage toward the upper first portion 14 of RD column 12. Suitable inert solvents include organic solvents that are unreactive with PAA and PO such as acetone, ethyl acetate, or benzene. When PAA is manufactured in a plant proximate to system 10, first feed line 30 may be a direct feed line from the PAA plant (not shown) to system 10. Since epoxidation is carried out in RD column 12, the feed stage can be used to control the amount of acetic acid present during the reaction and will thereby help to increase overall PO yield by reducing unwanted side reactions. Other operating parameters affecting the performance of the reactive distillation column, such as the reflux ratio, distillate to feed ratio, column pressure, and molar feed ratio of propylene to water can also be used to control the temperature in the RD column. In this regard, the RD column 12 is preferably operated within the temperature range of 20-150° C. and within a pressure range of 5-30 atmospheres.

The reaction between propylene and PAA occurs within the middle second portion 16 of the RD column 12 at a level below the entry point of first PAA feed line 30 and essentially on any stage below this entry point where both PAA and propylene are present. Unlike a liquid phase reactor, the heat of reaction in the reactive distillation column vaporizes the liquid that has the effect of controlling the temperatures and preventing hot spots from developing within the vertical column.

From the bottom third portion 18 of RD column 12, a portion of liquid products 26, which accumulate in the bottom as product B, is removed via the second products line 36 and is fed to first distillation column 40, which is an acetic acid separation column S1 where the co-product, acetic acid, is separated from the reaction mixture, and is recovered as a bottoms product $P_2$. The distillate $D_2$ of the first distillation column 40 is fed to second distillation column 50, which serves as a PO separation and recovery column. In this column the bottoms product, S, is a stream rich in solvent that can be reused in PAA production. The PO product $P_1$ is withdrawn as a side stream from second distillation column 50. The distillate product $D_3$, is composed primarily of propane and residual propylene from the original propylene stream fed to RD column 12.

The epoxidation reaction between propylene and PAA does not need a catalyst since PAA is a strong oxidizing agent; nevertheless, the reaction is preferably catalyzed with a homogenous catalyst that is introduced in the peracetic acid and/or propylene feeds 30, 32 or it can be introduced into the middle portion 16 of RD column 12 as a separate feed. It has been demonstrated that the addition of soluble Ferric acetylacetonate ($Fe^{3+}$ ions) at ppm level enhances the rate of formation of PO. The homogeneous catalyst in the form of dissolved $Fe^{3+}$ is used as the preferred catalyst in the manufacture of PAA and also increases the rate of the epoxidation reaction. PAA decomposition is enhanced by the presence of $Fe^{3+}$ and elevated temperatures; catalyst concentrations of greater than 5 ppm ferric ions is preferably avoided especially at high PAA feed concentrations and high reaction temperatures that exceed 60° C. It is expected that other transitional metal ions can be employed. Cobalt ions were found to exhibit similar catalytic activities to that of ferric ion but Co is more difficult to dispose of than iron.

Tributyl phosphate (TBP) or diethyl acid pyrophosphate (DAPP) was added to the prepared PAA feed solutions to stabilize the PAA before use in the epoxidation reaction.

When a stabilizer is used its concentration is typically 10 to 200 ppm. The DAPP is the preferred stabilizer at concentrations of about 60 ppm.

Modification of Epoxidation System with a Pre-Reactor

Figure 2:
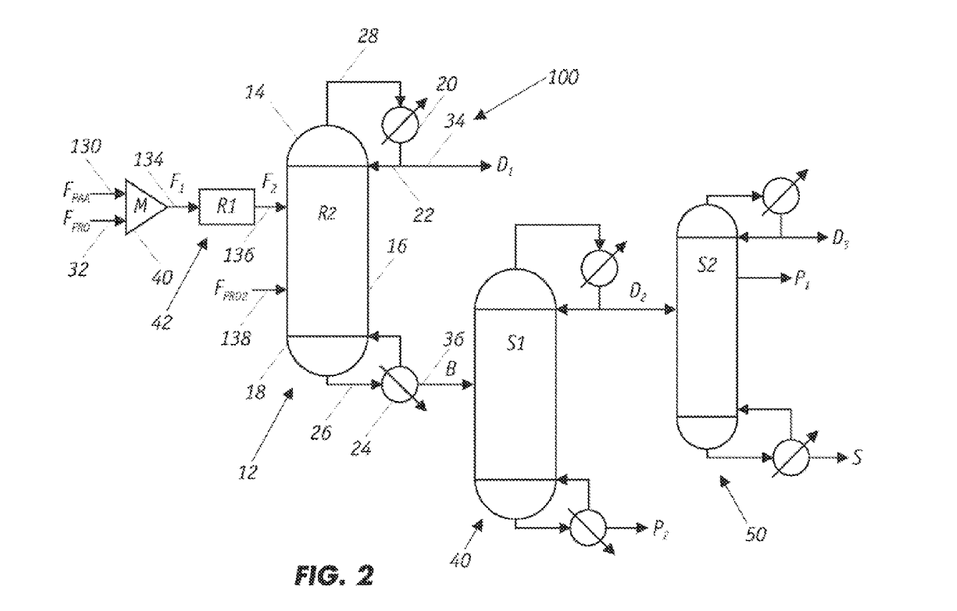
FIG. 2 is a schematic flow diagram of a reactive distillation process for producing propylene oxide implementing pre-mixing in a pre-reactor, separation of co-products, and recycling of starting materials.

FIG. 2 illustrates a second embodiment of the inventive continuous process wherein the epoxidation system 100 includes a mixer (M) 40 and pre-reactor (R1) 42 that are positioned upstream of the reactive distillation column (R2) 12. The pre-reactor 42 provides extra contact time of the reactants at low temperature to minimize PAA decomposition at higher temperatures and to ensure sufficient mixing and mass-transfer between PAA and propylene. This ensures high conversion of PAA and high selectivity to PO within RD column 12. Likewise, allowing a longer reaction time at lower temperatures throughout the RD column 12 should improve PO yields.

In operation, PAA and propylene are both fed into mixer 40 wherein PAA is fed as a solution in an inert solvent via first feed line ($F_{PAA}$) 130 and propylene is fed via second feed line ($F_{PRO}$) 132. The feed mixture $F_1$ (134) is fed into pre-reactor 42 where the reactants are in contact for a sufficient length of time before being transferred via line $F_2$ (136) into the middle second portion 16 preferably at a stage toward the upper first portion 14 of RD column 12. The RD column 12 is also equipped with an entry point for a supplemental propylene feed ($F_{PRO2}$) which is located in middle section portion 16 below the entry point for the feed line 136. The configuration and operations of the remaining parts of system 100 is preferably the same as that for system 10 as shown in FIG. 1 and described above.

Preferred Source of Peracetic Acid

A preferred method of preparing the PAA for use in the present invention oxidizes acetaldehyde with molecular oxygen in a solvent environment, where no water, hydrogen peroxide or sulfuric acid is present. It was determined that conventional techniques for synthesizing PAA by reacting acetic acid with hydrogen peroxide yielded impurities (including hydrogen peroxide, acetic acid, water, and sulfuric acid) that would be introduced into the reactive distillation column along with the feed. Using PAA containing such impurities would reduce the propylene oxide yield, as other propylene byproducts would also be produced. In addition, water reduces the solubility of propylene in the liquid reaction mixture and thus also lowers the rate of epoxidation. Instead, PAA is preferably manufactured by oxidizing acetaldehyde in a packed column reactor where the reactants flow downward concurrently. This one-step liquid-phase oxidation reaction is preferably catalyzed by $Fe^+$ ion in the form of ferric acetylacetonate, which is added to the acetaldehyde feed, and achieves a high yield (above 80%) with excellent selectivity (above 90%).

It has been shown that the same $Fe^{3+}$ ion is also useful as a catalyst for the epoxidation reaction of propylene with peracetic acid. The PAA is preferably prepared in solvents that are compatible, that is, inert in the subsequent epoxidation of propylene. A preferred solvent is ethyl acetate because of its relative ease of separation from propylene oxide. Subsequently, energy savings can be realized in the downstream purification of propylene oxide and separation of co-product acetic acid from the EA solvent. An alternative solvent is acetone. Thus the PAA synthesis process can be used in conjunction with the epoxidation and separation process for an integrated manufacturing process for the continuous production of PO.

EXAMPLES

Laboratory tests and process simulations confirmed the feasibility of conducting continuous epoxidation in a reactive distillation column. In particular, optimal operating conditions to maximize PO formation and to minimize byproduct formation were investigated by modeling the reaction and separation steps using ASPEN PLUS® simulation software from Aspen Technology, Inc. (Burlington, Mass.). The following examples relate to the preparation of PAA and its subsequent reaction with propylene to produce PO.

Comparison with Prior Art Peracetic Acid Epoxidation of Propylene

Typical equipment requirements and operating parameters for propylene oxide production in the epoxidation system 10 depicted in FIG. 1 are set forth in Table 1. The operating parameters were derived by simulation studies. As is apparent, the inventive process operates efficiently under mild conditions. The present invention compares favorably with the prior art processes for epoxidation of propylene, where conventional reactors and separation methodologies are used, such as the processes described by Phillips et al. in U.S. Pat. No. 2,785,185, Stautzenberger and Richey in U.S. Pat. No. 3,341,556, and the Daicel process described in U.S. Pat. No. 3,663,574 to Yamagishi et al.

For comparison, Table 1 also includes equipment and operating parameters for an actual commercial plant implementing the Daicel process for the same PO production capacity. The Daicel process requires a plurality of liquid phase reactors operating in series whereas the reactive distillation process needs only one reaction column and two distillation columns for the purification of propylene oxide and co-product acetic acid. Each reaction column in the Daicel process has its own condenser and associated separate plumbing including a cooling coil for temperature control. Furthermore, the Daicel process requires an additional absorption solvent for the recovery of peracetic acid from the product stream and additional distillation columns for the purification of propylene oxide. As a result the reactive distillation process requires a lower investment cost for capital equipment. In addition, with the present invention, the heat of reaction can be used efficiently in the RD column to reduce steam consumption in the reboiler and thereby reduce operating costs. The presence of vapor and liquid phases in the same space also eliminates the possibility of hot spots in the vertical RD column.

TABLE 1

| Parameter | Daicel Process | Present Process |
| --- | --- | --- |
| Equipment | plurality of concurrent reactors | reactive distillation column |
| Temperature control | cooling coil | no |
| Temperature (° C.) | 30-80 | 30 to 139 |
| Pressure (atm) | 8-11 | 8-18 |
| Molar feed ratio of propylene to peracetic acid | 1:1 to 6:1 | 3:1 to 15:1 |
| Feed peracetic acid concentration (weight %) | 30-34 | 15-30 |
| Acetic acid in feed (weight %) | 10-13 | 2 |
| Residence time (minutes) | 60-120 | 10 to 30/stage |

TABLE 1-continued

| Parameter | Daicel Process | Present Process |
|---|---|---|
| Conversion (mol %) | 93-99 | 100 |
| Catalyst | no | yes |
| PO Yield (mol %) | 87-90 | 76 to 83 |

Kinetics of Propylene Epoxidation by Peracetic Acid

Olefin reactivity in epoxidation reactions varies widely and depends on olefin size and structure. The relative reactivity of olefins with organic peracids is based on the ability of the peroxide oxygen of the per-acid (electrophilic) to be released in the presence of a nucleophilic group such as the double bond of an olefin. The more electron releasing groups near the double bond, the greater the nucleophilicity of the double bond, and, therefore, the greater the reaction rate of the olefin.

A kinetic reaction model was required to develop a reactive distillation process using the ASPEN PLUS simulation software. Rate data for the epoxidation of propylene by peracetic acid in ethyl acetate was obtained from laboratory experiments and were used to validate the kinetic model used. Rate data were obtained in the temperature range of 20 to 60° C. and pressures up to 128 psig with PAA dissolved in ethyl acetate at concentrations up to 14 wt % PAA and confirmed the dependence of the rate on both the peracetic acid and the propylene concentration.

The reaction proceeds via an intermediate complex between molecules of propylene and PAA and is given by:

$$r_{PO} = \frac{kK[CH_3COOOH][C_3H_6]^2}{1 + K[C_3H_6]^2} \quad (1)$$

where: $r_{PO}$=rate of formation of propylene oxide, mol L$^{-1}$ s$^{-1}$; k=first order rate constant, s$^{-1}$; K=equilibrium constant, L$^2$mol$^{-2}$; [CH$_3$COOOH]=PAA concentration, mol L$^{-1}$; and [C$_3$H$_6$]=propylene concentration, mol L$^{-1}$, with the temperature dependence of the rate following the Arrhenius equation:

$$k = Ae^{\frac{-E}{RT}} \quad (2)$$

where: A=preexponential factor=33,090, and E=activation energy=11.88 kcal/mol.

PAA decomposition rate, $r_d$, was observed to be first order with respect to PAA concentration:

$$r_d = k_1[CH_3COOOH] \quad (3)$$

with temperature dependence:

$$k_1 = A_1 e^{\frac{-E_1}{RT}} \quad (4)$$

where: $A_1$=preexponential factor=2.49×10$^{13}$, and $E_1$=activation energy=26.46 kcal/mol.

Example 1

Effect of Solvent Medium on Reactive Distillation Process

Suitable solvents for the epoxidation of the present invention must be unreactive in the reaction mixture and should have a significantly higher boiling point than that of PO for easy separation. It was found that the relative rate of epoxidation is insensitive to the choice of solvent from among acetone, ethyl acetate, and benzene. Results from the sensitivity analysis for a process for manufacturing 15% and 30% PAA solutions in acetone showed that PO and acetone were difficult to separate and therefore separation costs could be an important factor. Benzene is less desirable because of its high toxicity.

Simulations were performed comparing acetone and ethyl acetate as solvents in the PAA feed in the continuous reactive distillation system shown in FIG. 1 where similar operating conditions in the RD column 12 and AA distillation column 40 were used. The criterion for the PO distillation column 50 was that the unit operation achieved a minimum 95% recovery with a minimum purity of 95%. Table 2 lists the operating parameters and energy consumption for the process producing 200,000 tonnes/annum PO. The data show that in the case of acetone, 95% recovery and purity of PO can be achieved with a reboiler duty of 105457.7 kW and in the case of ethyl acetate 99% recovery and purity can be achieved with 98574.5 kW. In was found that to achieve 99% PO recovery and purity with acetone solvent could be prohibitively expensive; this is because the relative volatility of ethyl acetate to PO is higher than the relative volatility of acetone to PO.

TABLE 2

| | Value | |
|---|---|---|
| Parameter | Acetone | Ethyl acetate |
| Column pressure (atm) | 8 | 8 |
| Reflux ratio (RR) | 5.5 | 5.5 |
| Propylene:Peracetic acid molar feed ratio | 3:1 | 3:1 |
| Distillate to feed ratio (D/F) | 0.177 | 0.235 |
| Number of stages | 20 | 20 |
| Reaction stages | 5-16 | 5-16 |
| Liquid hold-up (m$^3$/stage) | 120 | 90 |
| Reaction stage temperature (° C.) | 26 to 99 | 32 to 91 |
| PO recovery and purity (%) | 95 | 99 |
| Total reboiler duty (kW) | 105457.7 | 98574.5 |

Example 2

Effect of Iron Catalyst Concentration on Rate of PO Formation

Batch rate data for the epoxidation of propylene by peracetic acid in ethyl acetate was obtained from laboratory experiments to determine the effect of catalyst concentration on the rate of PO formation. Experiments were performed at 60° C. and pressures of up to 130 psig. Table 3 shows the effect of the catalyst concentration on the rate constant, k, in Equation 1.

TABLE 3

| Catalyst [Fe$^{3+}$], ppm | k (min$^{-1}$) |
|---|---|
| 0 | 0.0102 |
| 0.4 | 0.0316 |
| 2.6 | 0.0331 |
| 5 | 0.0544 |
| 50 | Runaway |

The data suggest that the reaction rate constant increases up to five folds when the catalyst is present in the reaction mixture. A catalyst concentration of 50 ppm resulted in a runaway reaction with temperatures in excess of 120° C. and subsequent rapid increase in pressure. This indicates that the iron catalyst also enhances the PAA decomposition. Therefore dissolved iron concentrations that exceed 5 ppm $Fe^{3+}$ are to be avoided especially in high PAA concentration feeds and where reaction temperatures exceed 60° C.

Example 3

Positioning a Pre-Reactor Prior to RD Column

The continuous epoxidation system shown in FIG. 2 includes a pre-reactor (PR) 42 upstream from RD column 12. The PR provides extra contact time at low temperatures to minimize PAA decomposition and ensures sufficient mixing and mass-transfer between PAA and propylene. This ensures high conversion of PAA and high selectivity to PO. Based on 30 wt % PAA in an EA feed and similar operating conditions, a comparison of selected performance parameters for the continuous reactive distillation system with and without the pre-reactor is given in Table 4.

TABLE 4

| Parameter | RD Column | PR & RD Column |
|---|---|---|
| D/F | 0.23 | 0.23 |
| RR | 6.1 | 7 |
| Liquid hold-up (m³/stage) | 140 | 140 |
| PO Selectivity (%) | 79 | 83 |
| PAA Conversion (%) | 100 | 100 |

As is apparent, employing a pre-reactor in the combined RD column achieves a higher PO selectivity of 83% compared to the stand-alone RD column (79%) for this given set of operating conditions.

Example 4

Optimized Process Flowsheet

An optimized process flowsheet was derived through simulation for a 20,200 kg/year (51,300 lb/year) PO pilot plant based on a 30 wt % PAA feed stream in EA (with 2% acetic acid impurity) and 90% purity (mol %) propylene feed stream. (Process improvements are realized when running with 30 wt % peracetic acid feed instead of 15 wt %, as downstream purification costs of the co-product acetic acid and recovery of the solvent are reduced.) The flowsheet is based on a model including a decomposition term for PAA and a pre-reactor to the RD column. The pre-reactor is included as it allows for longer contact of PAA and propylene at lower temperatures. Propylene recycle is not included in the process flowsheet. The process was optimized for two scenarios:

Example 4a

Low conversion in the adiabatic, plug flow prereactor (PFR), high conversion and separation in the reactive distillation (RD) column.

Example 4b high conversion in the isothermal, plug flow prereactor (PFR) requiring cooling, and low conversion and separation in the reactive distillation column (RD). The operating conditions for Examples 4a and 4b are presented in Table 5.

TABLE 5

| | Example 4a | | Example 4b | |
|---|---|---|---|---|
| Parameter | PFR | RD Column | PFR | RD Column |
| Column pressure (atm) | 18 | 15 | 18 | 16 |
| Reflux ratio (RR) | — | 7 | — | 7 |
| Distillate to feed ratio (D/F) | — | 0.24 | — | 0.24 |
| Number of stages | — | 10 | — | 10 |
| Molar feed ratio (propylene:peracetic acid) | 2:1 | 4.9:1 | 2:1 | 7.4:1 |
| Feed stage: F1 | | 3 | | 3 |
| F2 | | 4 | | 4 |
| Reaction stages | — | 3-10 | — | 3-10 |
| Liquid hold-up (L/stage) | — | 15.75 | — | 6.75 |
| Residence time (min) | 16 | 253 | 61 | 142 |
| Reaction stage temperature (° C.) | 20-50 | 52-92 | 50 | 56-139 |
| Reboiler heat duty (kW) | — | 1.4 | −1.7 | 2.4 |
| PAA conversion (%) | 10.4 | 99.8 | 70.3 | 100 |
| PO selectivity (%) | 95.9 | 85.2 | 90.7 | 71.6 |
| Overall PO selectivity (%) | | 86.3 | | 85.0 |

The data indicates that maximum PO selectivity requires a longer time at cooler temperatures in the RD column so as to minimize PAA decomposition. In Example 4b the residence time (i.e. liquid holdup) in the RD column is decreased. However, while 100% PAA conversion is still achieved, selectivity to PO decreases to about 72%. The process flow diagram for obtaining the highest PO selectivity (Example 4a) is shown in epoxidation system with pre-reactor as shown FIG. 2, and the operating conditions for the process are given in Table 6. The designations R1, R2, S1 and S2 refer to the pre-reactor 42, reactive distillation column 12, distillation column S1 and distillation column S2, respectively, as shown in FIG. 2.

TABLE 6

| | Value | | | |
|---|---|---|---|---|
| Parameter | R1 | R2 | S1 | S2 |
| Pressure | 18 | 15 | 5 | 5 |
| RR | — | 7 | 2 | 70 |
| D/F | — | 0.24 | 0.82 | 0.45 |
| Reaction temperature (° C.) | 20 to 50 | 52-92 | — | — |

Figure 3:
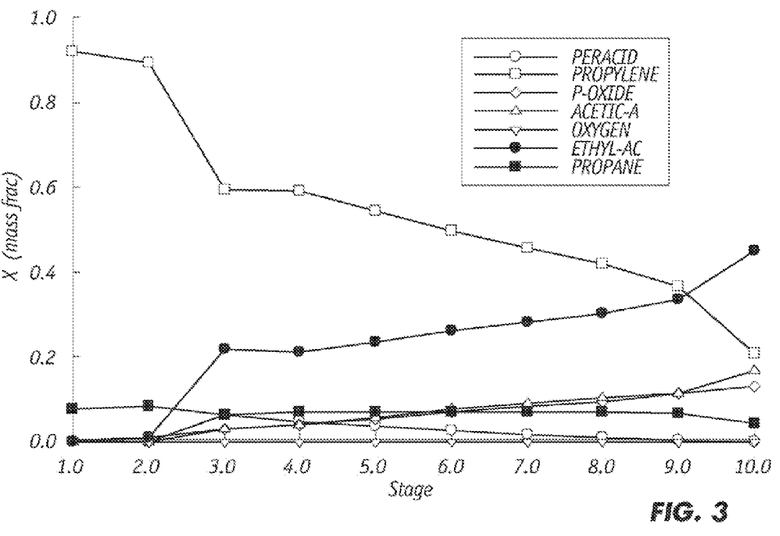
FIG. 3 shows the composition profiles in a reactive distillation column.
Figure 4:
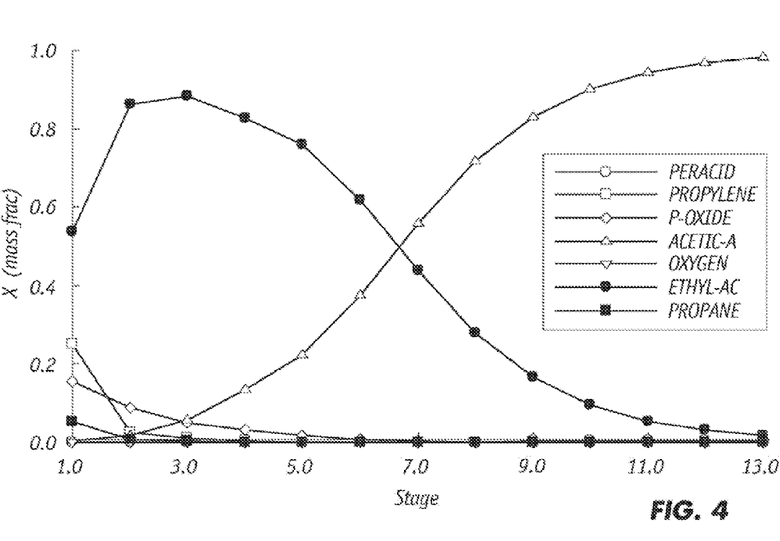
FIG. 4 shows the composition profiles in an acetic acid recovery column.
Figure 5:
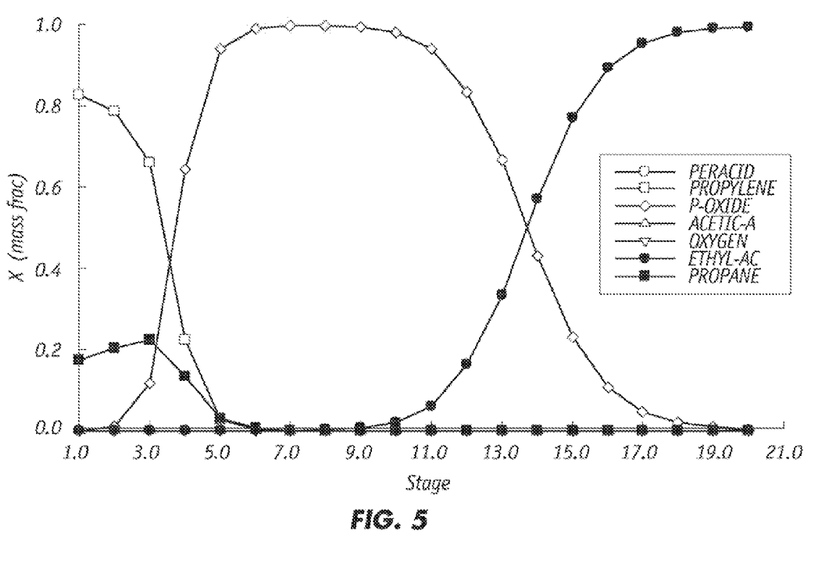
FIG. 5 shows the composition profiles in a propylene oxide separation and recovery column.

FIG. 3 shows the mass composition profile of peracetic acid, propylene, propylene oxide, acetic acid, oxygen, ethyl acetate, and propane on each stage in the reactive distillation column (R2). FIG. 4 shows the mass composition profile in the acetic acid recovery column (S1) achieving 98 wt % acetic acid purity in the product stream $P_2$. FIG. 5 shows the mass composition profile of peracetic acid, propylene, propylene oxide, acetic acid, oxygen, ethyl acetate, and propane in the propylene oxide recovery column (S2).

Table 7 provides a summary of the projected mass and mole flows and stream compositions for the 20,200 kg/year PO pilot plant that is equipped with a pre-reactor. The twelve process streams correspond to those that are depicted in FIG. 2. It will be recognized that further optimization may be achieved for different RD column designs, and for different operating requirements or conditions.

TABLE 7

| | $F_{PAA}$ | $F_{PRO}$ | $F_1$ | $F_2$ |
|---|---|---|---|---|
| Total Flow mol/hr | 147.77 | 107.47 | 255.24 | 255.35 |
| Total Flow kg/hr | 12.32 | 4.54 | 16.86 | 16.86 |

TABLE 7-continued

| Mass Frac | | | | |
|---|---|---|---|---|
| PERACID | 0.3288 | 0.0000 | 0.1904 | 0.1706 |
| PROPYLENE | 0.0000 | 0.9000 | 0.3789 | 0.3599 |
| P-OXIDE | 0.0000 | 0.0000 | 0.0000 | 0.0189 |
| ACETIC-A | 0.0278 | 0.0000 | 0.0161 | 0.0358 |
| OXYGEN | 0.0000 | 0.0000 | 0.0000 | 0.0004 |
| ETHYL-AC | 0.6434 | 0.0000 | 0.3725 | 0.3723 |
| PROPANE | 0.0000 | 0.1000 | 0.0421 | 0.0421 |

| | $F_{PRO2}$ | $D_1$ | B | $D_2$ |
|---|---|---|---|---|
| Total Flow mol/hr | 135.00 | 93.68 | 299.89 | 247.11 |
| Total Flow kg/hr | 5.71 | 3.92 | 18.65 | 15.46 |
| Mass Frac | | | | |
| PERACID | 0.0000 | 0.0000 | 0.0003 | 0.0000 |
| PROPYLENE | 0.9000 | 0.9030 | 0.3061 | 0.2498 |
| P-OXIDE | 0.0000 | 0.0003 | 0.1394 | 0.1571 |
| ACETIC-A | 0.0000 | 0.0000 | 0.1754 | 0.0020 |
| OXYGEN | 0.0000 | 0.0352 | 0.0001 | 0.0001 |
| ETHYL-AC | 0.0000 | 0.0000 | 0.3170 | 0.5384 |
| PROPANE | 0.1000 | 0.0614 | 0.0617 | 0.0527 |

| | $P_2$ | $D_3$ | $P_1$ | S |
|---|---|---|---|---|
| Total Flow mol/hr | 52.78 | 135.00 | 41.40 | 95.50 |
| Total Flow kg/hr | 3.19 | 5.71 | 2.40 | 8.38 |
| Mass Frac | | | | |
| PERACID | 0.0021 | 0.0000 | 0.0000 | 0.0000 |
| PROPYLENE | 0.0000 | 0.8957 | 0.0016 | 0.0000 |
| P-OXIDE | 0.0000 | 0.0000 | 0.9961 | 0.0037 |
| ACETIC-A | 0.9815 | 0.0000 | 0.0000 | 0.0036 |
| OXYGEN | 0.0000 | 0.0000 | 0.0000 | 0.0000 |
| ETHYL-AC | 0.0164 | 0.0000 | 0.0006 | 0.9927 |
| PROPANE | 0.0000 | 0.1043 | 0.0017 | 0.0000 |

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A continuous process for producing propylene oxide that comprises reacting propylene with peracetic acid in a reactive distillation column wherein propylene oxide is continuously produced by epoxidation of propylene in an inert solvent, wherein propylene oxide that is formed is continuously removed as a bottoms fraction comprising a reaction mixture from the reactive distillation column wherein the epoxidation and the distillation occur simultaneously in a single reaction column, and wherein heat generated by the epoxidation reaction between the propylene and peracetic acid vaporizes the reaction mixture within the reactive distillation column such that no cooling of the reaction mixture is required.

2. The process of claim 1 wherein reacting propylene with peracetic acid occurs in the presence of a homogeneous catalyst that is selected from the group consisting of transition metal ions and mixtures thereof.

3. The process of claim 2 wherein the homogeneous catalyst is selected from the group consisting of transition metal ions and mixtures thereof.

4. The process of claim 2 wherein the homogeneous catalyst comprises iron (III) ions.

5. The process of claim 2 wherein the homogeneous catalyst comprises ferric acetylacetonate.

6. The process of claim 1 wherein reacting propylene with peracetic acid is carried out in an inert solvent.

7. The process of claim 1 wherein the inert solvent is selected from the group consisting of ethyl acetate, acetone, benzene and mixtures thereof.

8. The process of claim 1 wherein the peracetic acid is introduced into the reactive distillation column as a solution containing 15-30 wt % peracetic acid in ethyl acetate.

9. The process of claim 1 comprising recovering a mixture containing propylene oxide, acetic acid and solvent as a bottoms fraction from the reactive distillation column and the process further comprises the steps of:
   (i) introducing the mixture into a first distillation zone, from which an acetic acid rich stream is recovered from the bottom and a propylene oxide rich stream is recovered from the overhead; and
   (ii) recovering propylene oxide from the propylene oxide rich stream.

10. The process of claim 9 further comprising the step of:
    (iii) introducing the propylene oxide rich stream into a second distillation zone and recovering a distillate stream rich in propylene, a middle stream rich in propylene oxide, and a bottoms stream rich in ethyl acetate.

11. The process of claim 1 wherein a prereactor is employed upstream of the reactive distillation column and propylene and peracetic acid are mixed in the prereactor before being transferred into the reactive distillation column.

12. The process of claim 1 wherein the reactive distillation column operates at a temperature range between 20 and 150° C. and a pressure range of 5 to 30 atm.

13. The process of claim 1 wherein the peracetic acid is produced by oxidizing acetaldehyde in the presence of an iron (III) catalyst.

14. A process for continuous epoxidation of propylene to produce propylene oxide in a vertical column by reactive distillation that comprises the steps of:
    (a) feeding propylene into the vertical column which includes a feed zone, a top zone and a bottom zone,
    (b) feeding a solution containing an inert solvent and peracetic acid into the vertical column;
    (c) concurrently in the vertical column which comprises a single reaction vessel, reacting the propylene and peracetic acid in an epoxidation reaction to form propylene oxide in the presence of a homogeneous catalyst that is selected from the group consisting of transition metal ions and mixtures thereof and recovering a mixture containing propylene oxide, acetic acid and solvent as a bottoms fraction from the bottom zone wherein heat generated by the epoxidation reaction via vaporizes a reaction mixture within the vertical column such that no cooling of the reaction mixture is required:
    (d) introducing the mixture into a first distillation zone, from which an acetic acid rich stream is recovered from the bottom and a propylene oxide rich stream is recovered from the overhead; and
    (e) introducing the propylene oxide rich stream into a second distillation zone and recovering a distillate stream rich in propylene, a middle stream rich in propylene oxide, and a bottoms stream rich in solvent.

15. The process of claim 14 comprising the step of feeding a solution containing the homogeneous catalyst into the vertical column.

16. The process of claim 14 wherein step (b) comprises feeding a solution containing peracetic acid.

17. The process of claim 16 wherein the solution includes an inert solvent.

18. The process of claim 14 wherein the inert solvent is selected from the group consisting of ethyl acetate, acetone, benzene and mixtures thereof.

19. The process of claim 14 wherein a prereactor is employed upstream of the vertical column and propylene and peracetic acid are mixed in the prereactor before being fed into the vertical column.

20. The process of claim 14 wherein the homogeneous catalyst comprises iron (III) ions.

21. The process of claim 20 wherein the homogeneous catalyst comprises ferric acetylacetonate.

22. The process of claim 20 wherein the peracetic acid fed in step (b) is produced by oxidizing acetaldehyde in the presence of an iron (III) catalyst.

23. The process of claim 14 wherein peracetic acid is introduced into the vertical column as a solution containing 15-30 wt % peracetic acid in ethyl acetate.

24. The process of claim 14 wherein the vertical column comprises a reactive distillation column that is a bubble column, a tray column wherein the propylene bubbles through a liquid reaction mixture, or a packed column.

25. The process of claim 14 wherein the vertical column operates at a temperature range between 20 and 150° C. and a pressure range of 5 to 30 atm.

* * * * *